(12) United States Patent
Chen et al.

(10) Patent No.: US 7,928,233 B2
(45) Date of Patent: Apr. 19, 2011

(54) SPIROINDOLINONE PYRIDINE DERIVATIVES

(75) Inventors: Li Chen, Shanghai (CN); Xingchun Han, Shanghai (CN); Song Yang, Shanghai (CN); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/685,748

(22) Filed: Jan. 12, 2010

(65) Prior Publication Data
US 2010/0204257 A1 Aug. 12, 2010

Related U.S. Application Data

(60) Provisional application No. 61/151,279, filed on Feb. 10, 2009.

(51) Int. Cl.
*C07D 401/04* (2006.01)
*A61K 31/438* (2006.01)

(52) U.S. Cl. .......................................... 546/18; 514/278
(58) Field of Classification Search ............... 546/18; 514/278
See application file for complete search history.

(56) References Cited

U.S. PATENT DOCUMENTS

| 7,495,007 | B2 | 2/2009 | Chen et al. | |
|---|---|---|---|---|
| 7,553,833 | B2 | 6/2009 | Liu et al. | |
| 7,638,548 | B2 | 12/2009 | Liu et al. | |
| 7,776,876 | B2 * | 8/2010 | Brimble et al. | ............... 514/299 |
| 2007/0213341 | A1 | 9/2007 | Chen et al. | |
| 2008/0009486 | A1 | 1/2008 | Chen et al. | |
| 2008/0114013 | A1 | 5/2008 | Liu et al. | |

FOREIGN PATENT DOCUMENTS

| EP | 0288847 | 11/1988 |
|---|---|---|
| EP | 0 947 511 A1 | 10/1999 |
| WO | 01/05790 | 1/2001 |
| WO | 2006091646 A2 | 8/2006 |
| WO | 2007104664 | 9/2007 |
| WO | 2007104714 | 9/2007 |
| WO | 2008080822 | 7/2008 |
| WO | 2008005268 A1 | 10/2008 |

OTHER PUBLICATIONS

Hans-Dieter Arndt, Dr. Kleine Molekule pp. 4664-4673—XP-002465843, 2006.
J. Amer. Chem. Soc. (2005) 127 p. 10130.
Howard C. Ansel, Pharmaceutical Dosage Forms and Drug Delivery Systems, 6th Ed. 1995, pp. 196, 456-457.
Ghosez, L., etal Tetrahedron 1995—11021-11042.
Lippa, B. et al Bioorganic & Med. Chem. Letters, 18 (11), 2008—3359-3363.
Ding et al, J. Med. Chem. (2006) 49:3432-3435.
Sairam, P., Elsevier 303-306, 2002.

* cited by examiner

*Primary Examiner* — Rita J Desai
(74) *Attorney, Agent, or Firm* — George W. Johnston; Patricia S. Rocha-Tramaloni

(57) ABSTRACT

There are provided compounds of the formula

I or a pharmaceutically acceptable salt, ester or enantiomer thereof
wherein W, X, Y, V, $R^1$ and $R^2$ are as described herein.
The compounds have utility as antiproliferative agents, especially, as anticancer agents.

4 Claims, No Drawings

SPIROINDOLINONE PYRIDINE DERIVATIVES

PRIORITY TO RELATED APPLICATION(S)

This application claims the benefit of U.S. Provisional Application No. 61/151,279, filed Feb. 10, 2009, which is hereby incorporated by reference in its entirety.

SUMMARY OF THE INVENTION

The present invention relates to pyridine analogues of spiroindolinones having the formula

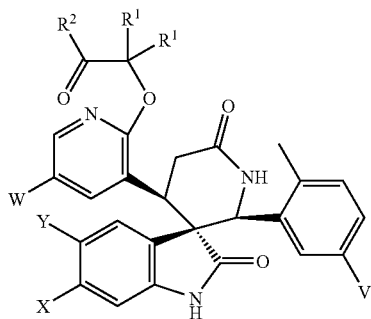

I or a pharmaceutically acceptable salt, ester or enantiomer thereof
wherein W, X, Y, V, $R^1$ and $R^2$ are as described herein.

The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am. Chem. Soc., 2005, 127, 10130 and also in US-2007-0213341-A1 published Sep. 13, 2007.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to spiroindolinones of the formula

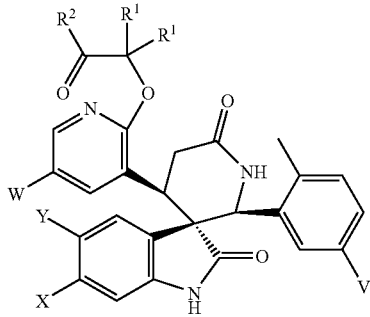

I wherein
is F, Cl or Br
Y is H or F
V is F or Cl
$R^1$ is Me, Et or nPr
$R^2$ is OH, OMe or $NHSO_2Me$
W is F, Cl or Br
or a pharmaceutically acceptable salt, ester or enantiomer thereof.

Further preferred are compounds of the formula
X is F, Cl or Br
Y is H
V is F or Cl
$R^1$ is Me or Et
$R^2$ is OH or $NHSO_2Me$ and
W is Cl.

Most preferred compounds are those of the formula:
racemic (2'S, 3S, 4'R)-6-chloro-4'-[5-chloro-2-(1-methoxy-carbonyl-1-methyl-ethoxy)-pyridin-3-yl]-2'-(5-fluoro-2-methyl-phenyl) spiro[3H-indole-3,3'-piperidine]-2,6' (1H)-dione;

racemic (2'S, 3S, 4'R)-6-chloro-4'-[5-chloro-2-(1-hydroxy-carbonyl-1-methyl-ethoxy)-pyridin-3-yl]-2'-(5-fluoro-2-methyl-phenyl) spiro[3H-indole-3,3'-piperidine]-2,6'(1H)-dione;

chiral (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione;

racemic (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione;

chiral (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione;

racemic (2'S, 3S, 4'R)-6-chloro-4'-[5-chloro-2-(1-methoxycarbonyl-1-methyl-ethoxy)-pyridin-3-yl]-2'-(5-chloro-2-methyl-phenyl) spiro[3H-indole-3,3'-piperidine]-2,6'(1H)-dione;

racemic (2'S, 3S, 4'R)-6-chloro-4'-[5-chloro-2-(1-hydroxy-carbonyl-1-methyl-ethoxy)-pyridin-3-yl]-2'-(5-chloro-2-methyl-phenyl) spiro[3H-indole-3,3'-piperidine]-2,6'(1H)-dione;

chiral (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione;

racemic (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione and chiral (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-2-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 456-457.

The compounds of formula I as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compound of formula I and are cleaved in vivo (in the organism) to the corresponding active carboxylic acid or alcohol respectively.

Synthesis

Compounds of this invention in formula I can be synthesized according to the following general schemes. It will be readily apparent to those of ordinary skill in the art that compounds in formula I can be prepared by substitution of the reagents or agents in the general synthesis routes. Using purification by chiral chromatography, compounds in formula I can be obtained as an optically pure or enriched enantiomers.

Scheme 1

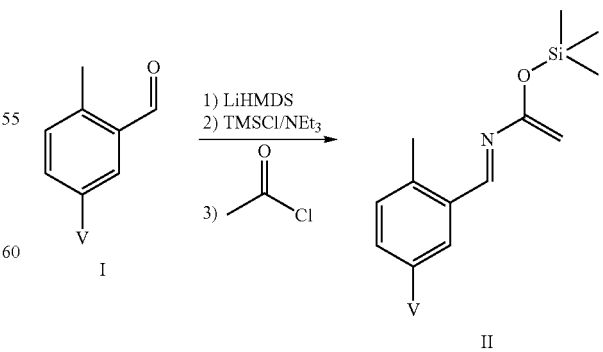

In general an appropriately selected aldehyde I can be reacted with lithium hexamethyldisilamide, chlorotrialkylsilane and acetyl chloride in a one-pot, multi-steps manner to generate 2-aza-1,3-butadiene II (Scheme 1) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

Scheme 2

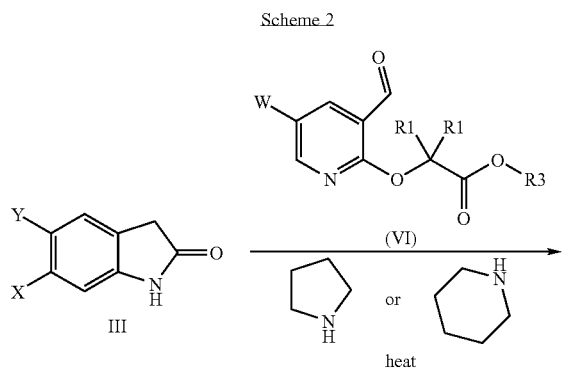

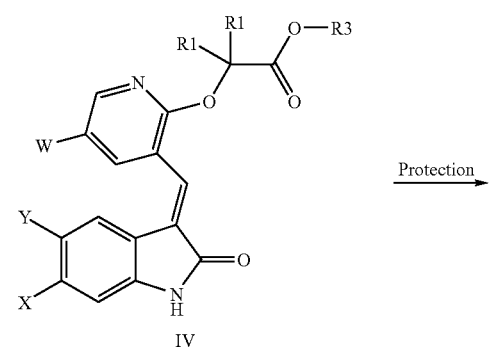

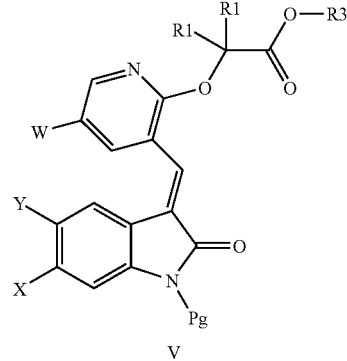

R1 is Me or Et or nPr, and R3 is lower alkyl

Oxindole III can be reacted with an appropriately substituted aldehyde VI in the presence of base under heated condition in either a protic like methanol, ethanol or an aprotic solvent like toluene, o-xylene to give intermediate IV. The commonly used base is either pyrrolidine or piperidine. Intermediate IV can be converted to intermediate V by a protection reaction. The protective group (Pg) can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc.

Scheme 3

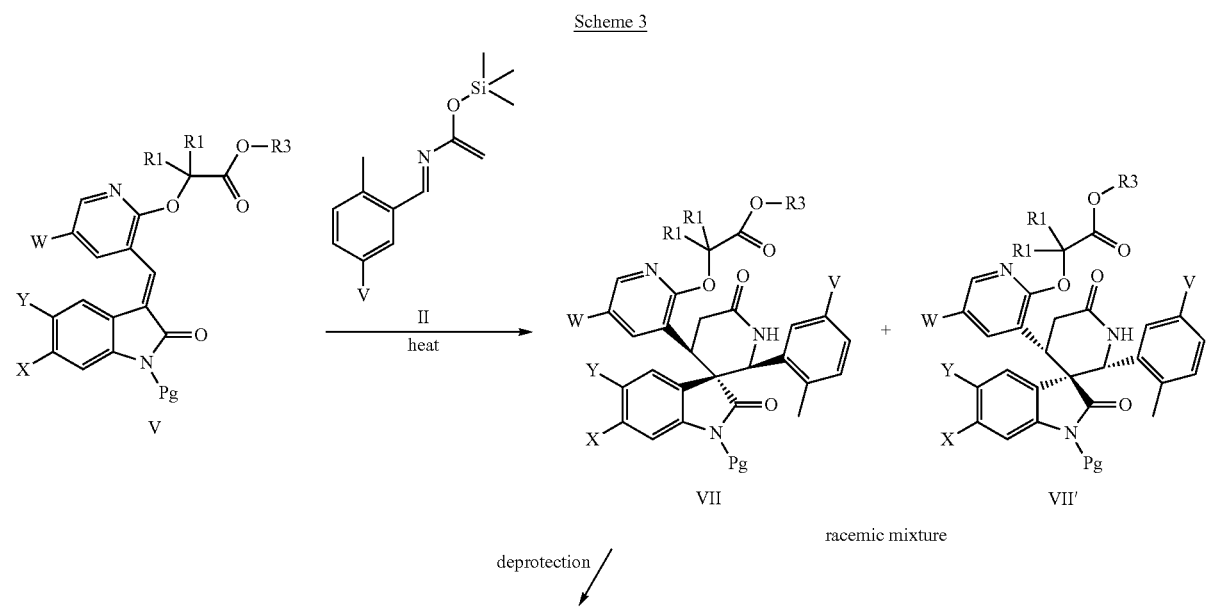

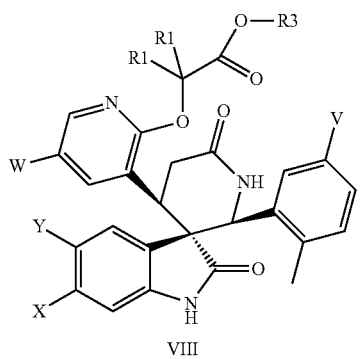

VIII

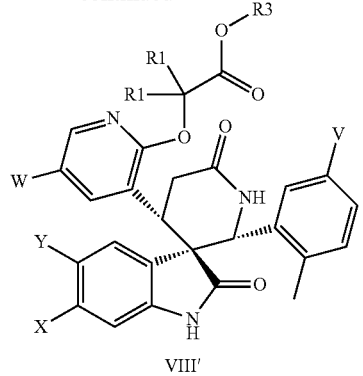

VIII' racemic mixture

R1 is Me or Et or nPr, and R3 is lower alkyl

Intermediate V can be reacted with a selected 2-aza-butadiene II prepared in Scheme 1 in toluene or o-xylene under heating from 110° C. to 160° C. and anhydrous condition to form intermediate VII and VII' as the major products shown as a racemic mixture of two enantiomers. A subsequent reaction to remove protective group (Pg) leads to various $R_2$ derivatized compound VIII and VIII'. (Scheme 3). In the case Pg is Boc group, Boc group can be removed by either trifluoroacetic acid or prolonged heating at a temperature between 110 to 116° C. during Aza Diels-Alder reaction between V and II without trifluoroacetic acid. Racemic mixture of VII and VII' or VIII and VIII' can be readily resolved into two chiral enantiomers by chiral Super Fluid Chromatography (SFC) or chiral HPLC or chiral column chromatography.

Scheme 4

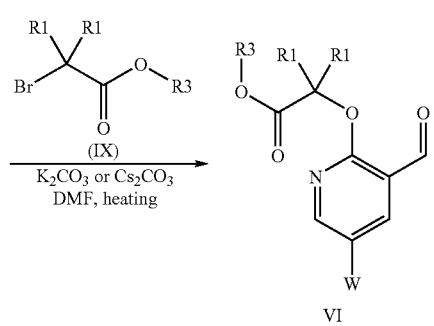

R1 is Me or Et or nPr, and R3 is lower alkyl intermediate VI in Scheme 2 can be prepared by treatment of aldehyde X, and reagent IX, a base like $K_2CO_3$ or $Cs_2CO_3$ in anhydrous N,N-dimethylformamide under heating conditions (Scheme 4). Aldehyde X and reagent IX can be commercially available or prepared according to methods established in literature procedures. Analogues XI and XII are prepared according to the methods illustrated in Scheme 5. Compound VIII is hydrolyzed to acid XI, followed by a coupling reaction using well-known methods to afford analogues XII. If R3 is not methyl group, XI can be converted into analogues XIII.

Scheme 5

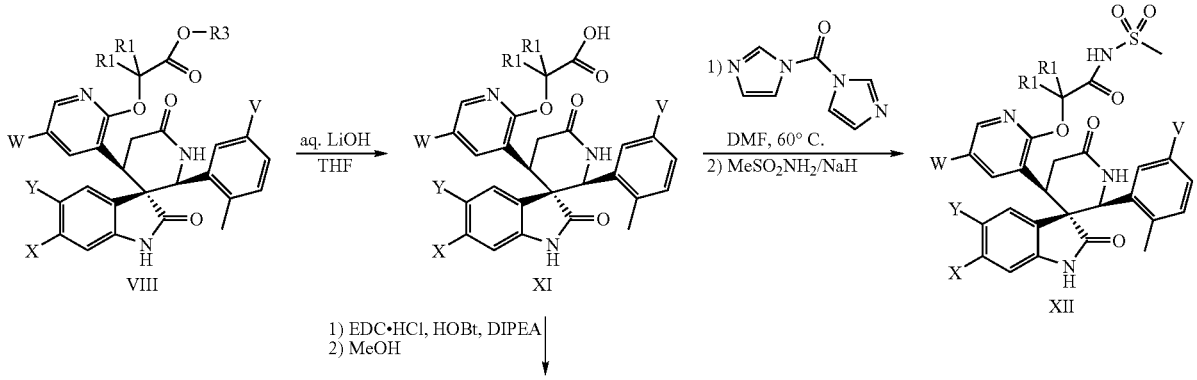

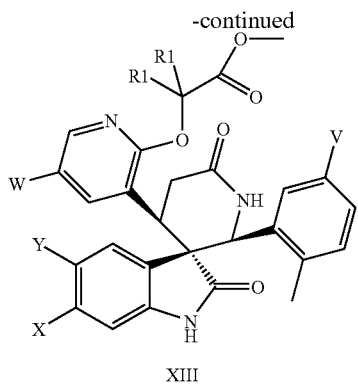

XIII

The following examples and references are provided to aid the understanding of the present invention, the true scope of which is set forth in the appended claims.

Example 1

Preparation of intermediate 3-bromo-5-chloro-pyridin-2-ol

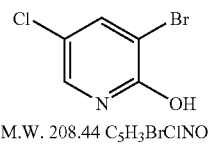

M.W. 208.44 C₅H₃BrClNO

At room temperature, bromine (1.2 mL, 24 mmol) was added dropwise to a solution of 5-chloro-2-pyridinol (2.9 g, 20 mmol) in glacial acetic acid (25 mL). After stirred at room temperature overnight, ethyl acetate and water were added. The organic layer was washed with water, dried and concentrated. The residue was triturated with diethyl ether and the precipitate was filtered and dried to give the title compound (1.5 g).

Example 2

Preparation of intermediate 5-chloro-2-hydroxy-pyridine-3-carbaldehyde

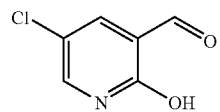

M.W. 157.56    C₆H₄ClNO₂

To a suspension of NaH (0.22 g, 60% dispersion in oil, 5.5 mmol) in anhydrous THF (20 mL) under argon atmosphere was added 3-bromo-5-chloro-pyridin-2-ol (1.03 g, 5 mmol) in a portionwise manner. After hydrogen evolution had ceased the mixture was cooled to −78° C. and tert-butyl lithium (10 mmol) was added at such a rate that the temperature did not rise above −65° C. The mixture was stirred for 5 mins then DMF (15 mmol) was added keeping the temperature below −50° C. The mixture was allowed to warm to room temperature and partitioned between ethyl acetate and 1N HCl. The organic layer was separated, washed with saturated NaCl, dried over anhydrous Na₂SO₄, filtered and concentrated to give the title compound (300 mg).

Example 3

Preparation of intermediate 2-(5-chloro-3-formyl-pyridin-2-yloxy)-2-methyl-propionic acid methyl ester

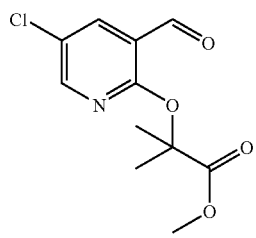

M.W. 257.68    C₁₁H₁₂ClNO₄

A mixture of 5-chloro-2-hydroxy-pyridine-3-carbaldehyde (8 g, 51 mmol), 2-bromo-2-methyl-propionic acid methyl ester (27.6 g, 153 mol), Cs₂CO₃ (28 g, 86.7 mol) in DMF (80 mL) was heated at 126° C. for 3 h. After cooled to room temperature, the mixture was poured into water and extracted with EtOAc. The organic layer was washed with water and brine, dried and concentrated. The residue was purified by flash column to give the title compound (6.2 g).

Example 4

Preparation of intermediate E/Z-2-[5-chloro-3-(6-chloro-2-oxo-1,2-dihydro-indol-3-ylidenemethyl)-pyridin-2-yloxy]-2-methyl-propionic acid methyl ester

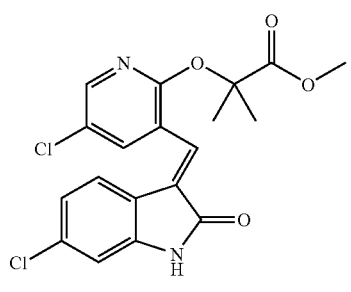

M.W. 407.26    C₁₉H₁₆Cl₂N₂O₄

To the mixture of 6-chlorooxindole (4.9 g, 29.3 mmol) and 2-(5-Chloro-3-formyl-pyridin-2-yloxy)-2-methyl-propionic acid methyl ester (7.2 g, 28 mmol) in methanol (50 mL) was added pyrrolidine (2.3 mL, 28 mmol) dropwise. The mixture was then heated at 70° C. for 1 h. After cooled to room temperature, the mixture was filtered and the precipitate was collected, dried to give title compound as a yellow solid (9 g).

Example 5

Preparation of intermediate E/Z-6-chloro-3-[5-chloro-2-(1-methoxycarbonyl-1-methyl-ethoxy)-pyridin-3-ylmethylene]-2-oxo-2,3-dihydro-indole-1-carboxylic acid tert-butyl ester

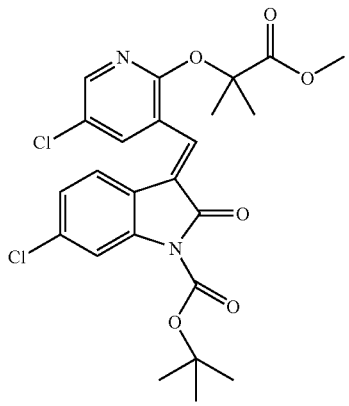

M.W. 507.37    $C_{24}H_{24}Cl_2N_2O_6$

To a solution of E/Z-2-[5-Chloro-3-(6-chloro-2-oxo-1,2-dihydro-indol-3-ylidenemethyl)-pyridin-2-yloxy]-2-methyl-propionic acid methyl ester (9 g, 0.022 mol) in dichloromethane (100 mL) at room temperature was added di-tert-butyl-dicarbonate (5.3 g, 0.024 mol), followed by the addition of 4-dimethylaminopyridine (1 g, 0.008 mol). After stirred at room temperature for 0.5 h, the mixture was concentrated. The residue was purified by flash column to give the title compound (11 g).

Example 6

Preparation of intermediate 1-(5-fluoro-2-methylphenyl)-3-trimethylsilyloxy-2-aza-1,3-butadiene

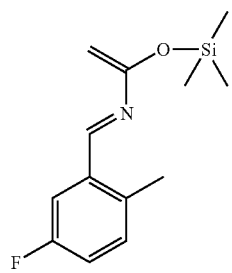

M.W. 251.38    $C_{13}H_{18}FNOSi$

To 1,1,1,3,3,3-hexamethyldisilazane (2.18 mL, 10.5 mmol) (Aldrich) under nitrogen at room temperature was added n-butyllithium (2.5 M, 4.2 mL, 10.5 mmol) (Aldrich). The reaction mixture was stirred at room temperature for 10 minutes. Then dry tetrahydrofuran (30 mL) was added, followed by the addition of 5-fluoro-2-methyl-benzaldehyde (1.38 g, 10 mmol) (Platte). After the mixture was stirred at room temperature for 0.5 h, trimethylsilyl chloride (1.33 mL, 10.5 mmol) (Aldrich) was added dropwise. Then the temperature of the mixture was lowered to 0° C. on a cooling ice bath. To this mixture was added triethylamine (1.9 mL, 13.6 mmol) in one portion, followed by the dropwise addition of a solution of acetyl chloride (0.97 mL, 13.6 mmol) in diethyl ether (50 mL). The cooling bath was removed, and the mixture was stirred at room temperature for 1 h. The mixture was quickly filtered on celite under nitrogen, and filtrate was concentrated under reduced pressure to give crude 1-(5-fluoro-2-methylphenyl)-3-trimethylsilyoxy-2-aza-1,3-butadiene as a yellow gum and used for the next step without further purification.

Example 7

Preparation of racemic (2'S, 3S, 4'R)-6-chloro-4'-[5-chloro-2-(1-methoxycarbonyl-1-methyl-ethoxy)-pyridin-3-yl]-2'-(5-fluoro-2-methyl-phenyl) spiro [3H-indole-3,3'-piperidine]-2,6'(1H)-dione

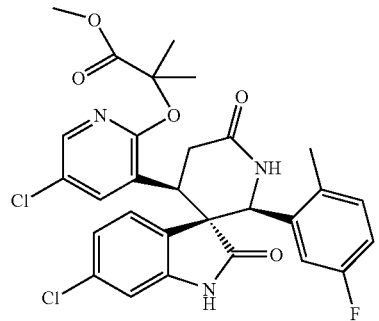

M.W. 586.45   $C_{29}H_{26}Cl_2FN_3O_5$

To a toluene solution (50 mL) of 1-(5-fluoro-2-methylphenyl)-3-trimethylsilyoxy-2-aza-1,3-butadiene (18 mmol) was added E/Z-6-chloro-3-[5-chloro-2-(1-methoxycarbonyl-1-methyl-ethoxy)-pyridin-3-ylmethylene]-2-oxo-2,3-dihydro-indole-1-carboxylic acid tert-butyl ester (3 g, 6 mmol). Then the reaction mixture were heated at 130° C. for 2 h. After the solution was cooled to room temperature, methanol was added, and then the mixture was concentrated. Then a mixture of trifluoroacetic acid (10 mL) and dichloromethane (30 mL) was added. The reaction mixture was stirred at room temperature for 10 min. The solution was concentrated and the residue was purified by Prep-HPLC to give title compound as a white solid (170 mg).

m/z (M+H)$^+$: 586

15

Example 8

Preparation of racemic (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione

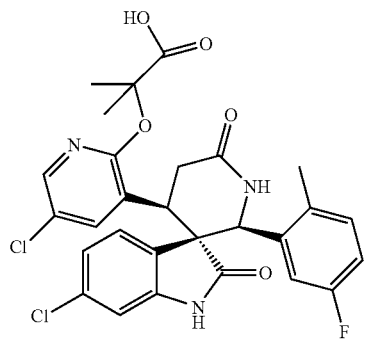

M.W. 572.418    $C_{28}H_{24}Cl_2FN_3O_5$

A mixture of racemic (2'S, 3S, 4'R)-6-chloro-4'-[5-chloro-2-(1-methoxycarbonyl-1-methyl-ethoxy)-pyridin-3-yl]-2'-(5-fluoro-2-methyl-phenyl) spiro[3H-indole-3,3'-piperidine]-2,6'(1H)-dione (160 mg, 0.27 mmol), LiOH.H$_2$O (250 mg, 5.94 mol), H$_2$O (5 mL) and methanol (15 mL) was heated at 80° C. for 40 min. After cooled to room temperature, the solution was acidified to "pH" 1 by addition of 1N HCl solution. The aqueous layer was extracted with EtOAc. The organic layer was washed with water, brine, dried over anhydrous Na$_2$SO$_4$ and concentrated to give the title compound as a light yellow solid (140 mg).

m/z (M+H)$^+$: 572

Example 9

Preparation of chiral (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione

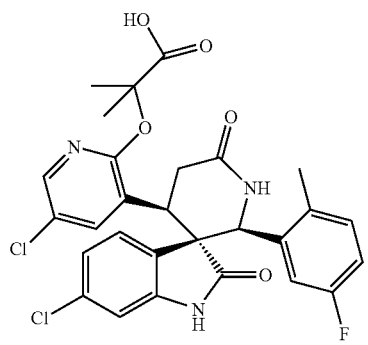

M.W. 572.418    $C_{28}H_{24}Cl_2FN_3O_5$

Separation of the two enantiomers from racemic (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione (50 mg), was conducted by chiral SFC to provide chiral (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione as a white solid (11 mg) and chiral (2'R, 3R, 4'S)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione as a white solid (10 mg).

m/z (M+H)$^+$: 572

Example 10

Preparation of racemic (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione

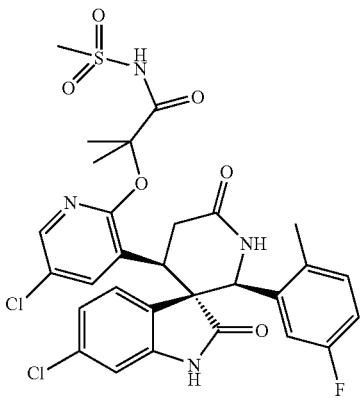

M.W. 649.52    $C_{29}H_{27}Cl_2FN_4O_6S$

A solution of racemic (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione (100 mg, 0.17 mmol) prepared in Example 8 and CDI (57 mg, 0.35 mmol) in DMF (1 mL) was heated at 60° C. for 2 h. Then to this solution was added a mixture of methanesulfonamide (129.2 mg, 1.36 mmol) and NaH (54.4 mg, 60%, 1.36 mmol) in DMF (2 mL), which had been stirred at room temperature for 2 h. After the resulting mixture was stirred at room temperature for 1 h, it was poured into water and the aqueous solution was acidified to "pH" 1-2 by addition of concentrated hydrochloride acid. After the aqueous phase was extracted with EtOAc twice, the combined organic phases were dried over anhydrous Na$_2$SO$_4$, concentrated and the residue was purified by flash column to give the title compound as a white solid (80 mg).

m/z (M+H)$^+$: 649

Example 11

Preparation of chiral (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione

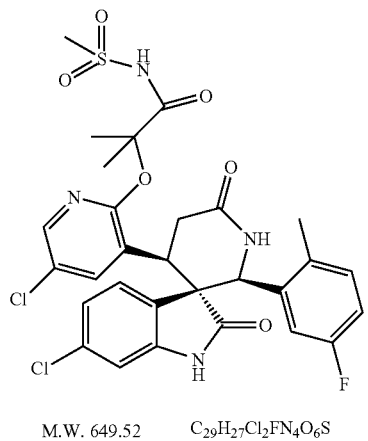

M.W. 649.52    $C_{29}H_{27}Cl_2FN_4O_6S$

Separation of the two enantiomers from racemic (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl)-spiro[3H-indole-3,3'-piperidine]-2,6'(1H)-dione (50 mg), was conducted by chiral SFC to provide chiral (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl)-spiro[3H-indole-3,3'-piperidine]-2,6'(1H)-dione as a white solid (19 mg) and chiral (2'R, 3R, 4'S)-4'-[5-chloro-2-(2-methanesulfonylamino-1,1-methyl-2-oxo-ethoxy)-pyridin-3-yl]-6-chloro-2'-(5-fluoro-2-methyl-phenyl)-spiro[3H-indole-3,3'-piperidine]-2,6'(1H)-dione as a white solid (18 mg).

m/z (M+H)$^+$: 649

Example 12

Preparation of intermediate 1-(5-chloro-2-methyl-phenyl)-3-trimethylsilyoxy-2-aza-1,3-butadiene

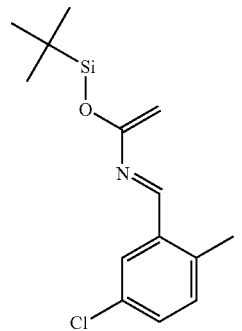

M.W. 281.86    $C_{14}H_{20}ClNOSi$

To dry tetrahydrofuran (100 mL) was added 1M THF solution of LiHMDS (97 mmol, 97 mL) under Ar at room temperature, followed by the addition of 5-chloro-2-methyl-benzaldehyde (15 g, 97 mmol). After the mixture was stirred at room temperature for 1 h, trimethylsilyl chloride (12.3 mL, 97 mmol) was added dropwise. Then the temperature of the mixture was lowered to 0° C. on a cooling ice bath. To this mixture was added triethylamine (17.6 mL, 126 mmol) in one portion, followed by the dropwise addition of a solution of acetyl chloride (9 mL, 126 mmol) in diethyl ether (200 mL). The cooling bath was removed, and the mixture was stirred at room temperature overnight. The mixture was quickly filtered on celite under nitrogen, and filtrate was concentrated under reduced pressure to give crude 1-(5-chloro-2-methyl-phenyl)-3-trimethylsilyoxy-2-aza-1,3-butadiene as a yellow gum and used for the next step without further purification.

Example 13

Preparation of racemic (2'S, 3S, 4'R)-6-chloro-4'-[5-chloro-2-(1-methoxycarbonyl-1-methyl-ethoxy)-pyridin-3-yl]-2'-(5-chloro-2-methyl-phenyl) spiro [3H-indole-3,3'-piperidine]-2,6'(1H)-dione

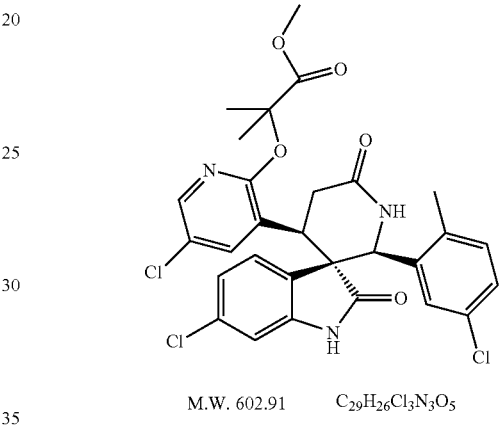

M.W. 602.91    $C_{29}H_{26}Cl_3N_3O_5$

In a manner similar to the method described in Example 8, E/Z-6-chloro-3-[5-chloro-2-(1-methoxycarbonyl-1-methyl-ethoxy)-pyridin-3-ylmethylene]-2-oxo-2,3-dihydro-indole-1-carboxylic acid tert-butyl ester (3 g, 6 mmol) prepared in Example 5 was reacted with 1-(5-chloro-2-methylphenyl)-3-trimethylsilyoxy-2-aza-1,3-butadiene (17 mmol) in toluene and then trifluoroacetic acid in dichloromethane to give the title compound as a white solid (200 mg).

m/z (M+H)$^+$: 602

Example 14

Preparation of racemic (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro [3H-indole-3,3'-piperidine]-2,6'(1H)-dione

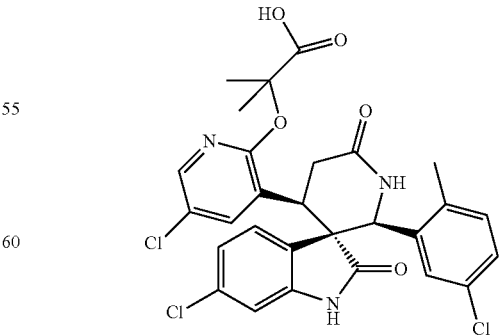

M.W. 588.88    $C_{28}H_{24}Cl_3N_3O_5$

A mixture of racemic (2'S, 3S, 4'R)-6-chloro-4'-[5-chloro-2-(1-methoxycarbonyl-1-methyl-ethoxy)-pyridin-3-yl]-2'-(5-chloro-2-methyl-phenyl) spiro[3H-indole-3,3'-piperidine]-2,6'(1H)-dione (200 mg, 0.33 mmol), LiOH.H$_2$O (280 mg, 6.6 mmol), H$_2$O (5 mL) and methanol (15 mL) was heated at 80° C. for 40 min. After cooled to room temperature, the solution was acidified to "pH" 1 by addition of 1N HCl solution. The aqueous layer was extracted with EtOAc. The organic layer was washed with water, brine, dried over anhydrous Na$_2$SO$_4$ and concentrated to give the title compound as a light yellow solid (200 mg).

m/z (M+H)$^+$: 588

Example 15

Preparation of chiral (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione

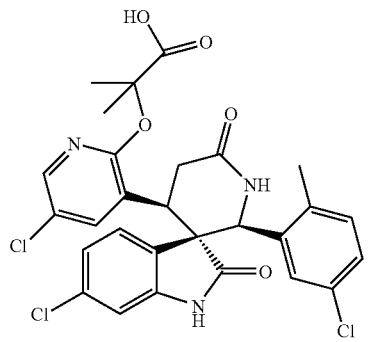

M.W. 588.88    C$_{28}$H$_{24}$Cl$_3$N$_3$O$_5$

Separation of the two enantiomers from racemic (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione (60 mg), was conducted by chiral SFC to provide chiral (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione as a white solid (20 mg) and chiral (2'R, 3R, 4'S)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione as a white solid (21 mg).

m/z (M+H)$^+$: 588

Example 16

Preparation of racemic (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione

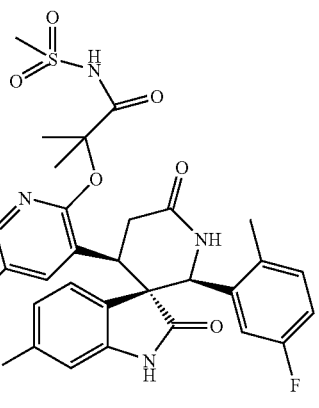

M.W. 665.98    C$_{29}$H$_{27}$Cl$_3$N$_4$O$_6$S

A solution of racemic (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione (100 mg, 0.17 mmol) prepared in Example 14 and CDI (57 mg, 0.35 mmol) in DMF (1 mL) was heated at 60° C. for 2 h. Then to this solution was added a mixture of methanesulfonamide (129.2 mg, 1.36 mmol) and NaH (54.4 mg, 60%, 1.36 mmol) in DMF (2 mL), which had been stirred for 2 h at room temperature. After the resulting mixture was stirred at room temperature for 1 h, it was poured into water and the aqueous solution was acidified to "pH" 1-2 by addition of concentrated hydrochloride acid. After the aqueous phase was extracted with EtOAc twice, the combined organic phases were dried over anhydrous Na$_2$SO$_4$, concentrated and the residue was purified by flash column to give the title compound as a white solid (80 mg).

m/z (M+H)$^+$: 665

Example 17

Preparation of chiral (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione

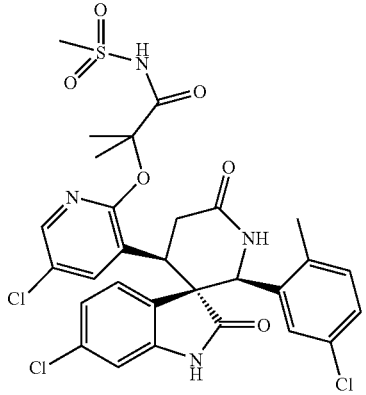

M.W. 665.98    C$_{29}$H$_{27}$Cl$_3$N$_4$O$_6$S

Separation of the two enantiomers from racemic (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione (50 mg), was conducted by chiral SFC to provide chiral (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione as a white solid (19 mg) and chiral (2'R, 3R, 4'S)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione as a white solid (18 mg).

m/z (M+H)$^+$: 665

Example 18

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 μM.

Representative values are, for example:

| Example | $IC_{50}$ (μM, 0.02% BSA) |
|---|---|
| 8 | 0.145 |
| 9 | 0.108 |
| 11 | 0.135 |
| 15 | 0.056 |

What is claimed:

1. A compound of the formula

I wherein
X is F, Cl or Br
Y is H or F
V is F or Cl
$R^1$ is Me, Et or nPr
$R^2$ is OH, OMe or $NHSO_2Me$
W is F, Cl or Br
or a pharmaceutically acceptable salt, ester or enantiomer thereof.

2. The compound of claim 1 wherein
X is F, Cl or Br
Y is H
V is F or Cl
$R^1$ is Me or Et
$R^2$ is OH or $NHSO_2Me$ and
W is Cl.

3. A compound of claim 1 selected from the group consisting of
racemic (2'S, 3S, 4'R)-6-chloro-4'-[5-chloro-2-(1-methoxycarbonyl-1-methyl-ethoxy)-pyridin-3-yl]-2'-(5-fluoro-2-methyl-phenyl) spiro[3H-indole-3,3'-piperidine]-2,6'(1H)-dione;
racemic (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione;
chiral (2'S, 3S, 4'R)-6-chloro-4'-[5-chloro-2-(1-hydroxycarbonyl-1-methyl-ethoxy)-pyridin-3-yl]-2'-(5-fluoro-2-methyl-phenyl) spiro[3H-indole-3,3'-piperidine]-2,6'(1H)-dione;
racemic (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione;
chiral (2'S, 3S, 4'R)-4'-[5-chloro-2-(2-methanesulfonylamino-1,1-methyl-2-oxo-ethoxy)-pyridin-3-yl]-6-chloro-2'-(5-fluoro-2-methyl-phenyl) spiro[3H-indole-3,3'-piperidine]-2,6'(1H)-dione;
racemic (2'S, 3S, 4'R)-6-chloro-4'-[5-chloro-2-(1-methoxycarbonyl-1-methyl-ethoxy)-pyridin-3-yl]-2'-(5-chloro-2-methyl-phenyl) spiro[3H-indole-3,3'-piperidine]-2,6'(1H)-dione;
racemic (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione;
chiral (2'S, 3S, 4'R)-6-chloro-4'-[5-chloro-2-(1-hydroxycarbonyl-1-methyl-ethoxy)-pyridin-3-yl]-2'-(5-chloro-2-methyl-phenyl) spiro[3H-indole-3,3'-piperidine]-2,6'(1H)-dione;
racemic (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione and
chiral (2'S, 3S, 4'R)-4'-[5-chloro-2-(2-methanesulfonylamino-1,1-methyl-2-oxo-ethoxy)-pyridin-3-yl]-6-chloro-2'-(5-chloro-2-methyl-phenyl)-spiro[3H-indole-3,3'-piperidine]-2,6'(1H)-dione.

4. A pharmaceutical composition comprising a compound of the formula

I wherein
X is F, Cl or Br
Y is H or F
V is F or Cl
$R^1$ is Me, Et or nPr
$R^2$ is OH, OMe or $NHSO_2Me$
W is F, Cl or Br
or a pharmaceutically acceptable salt, ester or enantiomer thereof together with a pharmaceutically acceptable carrier or excipient.

* * * * *